United States Patent [19]

Olbrich et al.

[11] Patent Number: 5,959,115
[45] Date of Patent: Sep. 28, 1999

[54] PROCESS FOR THE PREPARATION OF PURE FLUPIRTINE MALEATE AND ITS A MODIFICATION

[75] Inventors: Alfred Olbrich, Halle/Westf.; Peter Emig, Bruchköbel; Bernhard Kutscher, Maintal; Karl-Friedrich Landgraf, Dresden; Siegfried Pauluhn, Walldürn-Reinhardsachsen; Hans Stange, Riesa, all of Germany

[73] Assignee: ASTA Medica Aktiengesellschaft, Dresden, Germany

[21] Appl. No.: 09/064,790

[22] Filed: Apr. 23, 1998

[30] Foreign Application Priority Data

Apr. 23, 1997 [DE] Germany .................. 197 16 984

[51] Int. Cl.⁶ .................................................. C07D 213/75
[52] U.S. Cl. .............................................................. 546/308
[58] Field of Search ............................................. 546/308

[56] References Cited

U.S. PATENT DOCUMENTS 4,481,205  11/1984  von Bebenburg et al. ............. 546/307

FOREIGN PATENT DOCUMENTS 31 33 519   6/1982   Germany .

OTHER PUBLICATIONS

S. Schwoch et al., 2,3–Dihydrospiro'1H–4–an 5–azabenzimidazole–2, 1'–cyclohexane!: Reactions with nucleophiles, Helvetica Chimica Acta, vol. 77, 1994, pp. 2175–2190.

Primary Examiner—Zinna Northington Davis
Attorney, Agent, or Firm—Pillsbury Madison & Sutro LLP

[57] ABSTRACT

A process for preparation of pure flupertine maleate and the pure A crystalline form of flupertine maleate by the use of water soluble alcohols during synthesis and/or purification.

11 Claims, 11 Drawing Sheets

PROCESS FOR THE PREPARATION OF PURE FLUPIRTINE MALEATE AND ITS A MODIFICATION

BACKGROUND OF THE INVENTION

1. Field of the Invention

The present invention relates to a process for the preparation of pure flupirtine maleate and the pure A crystal modification of flupirtine maleate.

2. Background Information

Flupirtine maleate is 2-amino-3-carbethoxyamino-6-(p-fluorobenzylamino)pyridine maleate (I). This compound is commercially available under the trade name Katadolon® and is used in particular as an analgesic.

The preparation of flupirtine maleate is described in DE 31 33 519.

2-amino-3-nitro-6-(4-fluorobenzylamino)pyridine (ANFP) is dissolved in 2-methoxyethanol and is hydrogenated with hydrogen in the presence of Raney nickel at 5 bar and 60° C. to give 2,3-diamino-6-(4-fluorobenzyl-amino)pyridine. This is acylated with ethyl chloroformate and triethylamine under inert gas to give flupirtine base. The catalyst is filtered off and a solution of isopropanol and maleic acid is added directly to the filtrate which contains triethylamine hydrochloride, crude flupirtine maleate being precipitated with vigorous stirring under an inert-gas atmosphere.

Since it became known that the solvent 2-methoxyethanol used for the hydrogenation of ANFP is associated with a health risk owing to its considerable potential danger in the urogenital region, this compound is an unacceptable solvent for this reaction on the industrial scale.

During the precipitation of flupirtine maleate from the parent base, the avoidance of troublesome coloured complexes induced by atmospheric oxygen is of decisive importance. According to the colour intensity, they may very greatly impair the further purification up to on-spec flupirtine maleate.

The exclusion of atmospheric oxygen by an intensive supply of inert gas and a closed reactor system is therefore absolutely essential in this reaction step.

In a very time-consuming and inconvenient purification process, crude flupirtine maleate is converted into crude flupirtine base by liberation with ammonia or sodium hydroxide solution. The liberation process gives ammonium or sodium salts which pollute the waste water and constitute a troublesome accompanying phenomenon from the ecological point of view. The crude flupirtine base is recrystallized from isopropanol and, after clarification with activated carbon/kieselguhr, is reacted with a solution of maleic acid in isopropanol to give pure flupirtine maleate.

The complicated process used to date can be illustrated by the following reaction scheme:

A: ANFP→hydrogenation→acylation→crude flupirtine base I

B: crude flupirtine base I→maleic acid→crude flupirtine maleate

C: crude flupirtine maleate→liberation→crude flupirtine base II

D: crude flupirtine base II→recrystallization→pure flupirtine base

E: pure flupirtine base→maleic acid→modification→pure flupirtine maleate where reaction steps C–E are required purification steps without which pure, uniform and on-spec pure maleate could not be obtained. They are very labour-intensive and expensive purification operations, considerably lengthen the synthesis process and lead to an on-spec pure flupirtine maleate only by a complicated and inconvenient route which is very expensive in terms of production technology.

The extremely large reactor volumes which are required for the crystallization of the flupirtine base and for the precipitation of the flupirtine maleate and tie up a considerable amount of production capacity are considered a further criterion indicating a very high level of technical complexity in the purification steps C and E.

By metric ton of flupirtine maleate, 25 t of waste solution which contain 2-methoxyethanol, isopropanol, ammonia, ammonium maleate and water must be disposed of by incineration.

This procedure is very uneconomical and difficult to handle and furthermore does not meet the requirements for environmentally acceptable production.

The flupirtine maleate is generally obtained as a mixture of 2 crystal modifications A and B, these being present in the mixture in different ratios.

Such mixtures present a major problem with regard to further pharmaceutical processing. In particular, this has an adverse effect with regard to maintaining constant pharmaceutical production conditions and hence with respect to guaranteeing the pharmaceutical quality of an active ingredient. These different mixtures of crystal modifications lead to different release rates during release from the pharmaceutical formulation in the human body. This deficiency may delay the onset of action of flupirtine maleate as the active ingredient and hence falsify the activity balance.

SUMMARY OF THE INVENTION

It is thus the object of the invention to develop a simple, environmentally acceptable process for the preparation of pure flupirtine maleate from which the pure A modification can be obtained by crystal modification.

According to the invention, the object is achieved by carrying out the hydrogenation of 2-amino-3-nitro-6-(4-fluorobenzylamino)pyridine (ANFP) in the presence of Raney nickel, acylation of the intermediate 2,3-diamino-6-(4-fluorobenzylamino)pyridine (DAFP) with ethyl chloroformate and the reaction of the resulting flupirtine base with maleic acid in water-soluble alcohols, such as ethanol or isopropanol.

The following process variants are possible:

1st process variant:

A: ANFP→hydrogenation→acylation→crude flupirtine base

B: crude flupirtine base→maleic acid→crude flupirtine maleate

C–E: not applicable

F: crude maleate→pure maleate

The dissolved and very oxygen-sensitive crude base synthesized in situ in process step A was converted by a very rapid suction filtration process into an aqueous maleic acid solution from which crude flupirtine maleate having far less colour than the earlier product is immediately precipitated with stirring. After crystallization in isopropanol-water, said crude flupirtine maleate gave an on-spec pure maleate in about 85% yield.

This dramatic shortening of the preparation process for flupirtine maleate in comparison with the processes practised to date, with bypassing of the process steps C–E, makes it possible to obtain the pure maleate directly from the crude flupirtine maleate and to eliminate the troublesome colour problems in the flupirtine preparation at an early stage.

2nd process variant:
- A: ANFP→hydrogenation→acylation→crude flupirtine base
- B: flupirtine base→maleic acid→crude flupirtine maleate
- C–F: not applicable
- G: without isolation of the crude maleate→pure maleate As compared with process step F, process step G represents a substantially shorter alternative process in which the precipitation of crude flupirtine maleate from the flupirtine base formed in situ in isopropanol is effected by filtration with suction into an aqueous maleic acid solution at 50–60° C. and, after crystal modification, colourless pure flupirtine maleate is obtained in 85–90% yield.

3rd process variant:
- A: ANFP→hydrogenation→acylation→crude flupirtine base (isolated)
- B: pure flupirtine base→maleic acid→pure flupirtine maleate Here, after acylation is complete, the flupirtine base is precipitated preferably in ethanol or water and is purified by simple recrystallization. The preparation of the pure flupirtine maleate is then carried out analogously to the process variants mentioned.

It was completely surprising that both the hydrogenation of ANFP and the acylation of the DAFP formed with ethyl chloroformate can be carried out in water-soluble alcohols, such as ethanol or isopropanol.

Here, precipitation in aqueous maleic acid solution gives a nickel-free flupirtine maleate which no longer need be subjected to a complicated, multistage purification process.

The fact that for the first time a white product free of coloured complexes was obtained in the precipitation of crude flupirtine maleate, so that here too no additional purification operations are required, proved to be a further advantage.

In the subsequent crystal modification to obtain the pure A modification of flupirtine maleate, it was found, totally surprisingly, that mixtures of the two modifications A and B of flupirtine maleate can be converted into a single-phase flupirtine maleate consisting only of the A modification under certain conditions by stirring.

A high proportion of the A modification in the starting sample, high solids concentration in the suspension (1:1 to 1:0.8) and temperatures in the range from −10 to 60° C. have proved particularly advantageous.

At high solids concentration (1:1) and temperatures between 20 and 60° C., however, it was also possible to convert flupirtine maleate present predominantly in the B modification (90% of B) completely into the A modification in stirring times of 2 to 5 hours, the fact that the establishment of the desired crystal modification A can also be achieved at temperatures of 0 to 30° C. having been found as a particularly surprising advantage.

If these discoveries are applied to the precipitation process (combination of flupirtine base and maleic acid in a suitable solvent), the conditions required according to prior art for achieving a very high primary proportion of the A modification will first be maintained but then the complete conversion of B fractions present into the A modification will be ensured by an appropriately performed stirring process.

Expediently, the stirring process will follow directly after the precipitation, that is to say that, beginning during the cooling, the stirring is also continued after cooling to room temperature until the conversion is complete. The solids concentration is kept as high as possible.

Surprisingly, previously unknown crystallized solvates of flupirtine maleate were found during the recrystallization and precipitation, both in isopropanol and in ethanol.

The solvates observed in the crystal suspensions are converted into the A modification during the stirring process. On the other hand, no solvate or hydrate formation is observed when crystals dried beforehand to constant weight are dispersed in isopropanol, ethanol or water. The solvates were observed only during the primary crystallization (nucleation).

Furthermore, it was found that predried crystals which are freed from externally adsorbed solvent but still contain solvent bound internally within the crystal can be converted into the B modification by heating to temperatures of about 80–100° C. Subsequent formation of the B modification from solvate during the technical drying is prevented by sufficiently long stirring of the crystal suspension after the maleate precipitation.

BRIEF DESCRIPTION OF THE DRAWINGS

FIG. 1 (lower portion) shows the X-ray diffraction patterns of modifications A and B.

DETAILED DESCRIPTION OF THE INVENTION

Phase Analysis

The crystallized phases of flupirtine maleate, modifications A and B and isopropanol and ethanol solvate were determined by X-ray diffraction using a powder diffractometer. In this method, a transformed image of the crystal structure or structures present is obtained, which image is formed by summation of the diffraction effects at a very large number of crystals. This method is therefore particularly suitable for determining the composition of mixtures consisting of different crystallized phases. Fresh, still solvent-moist samples can also be investigated by this method. Furthermore, structural changes associated with phase transitions can be directly observed.

Method: X-ray Diffractometry

Diffraction Patterns of Modifications A and B

Figure 1:
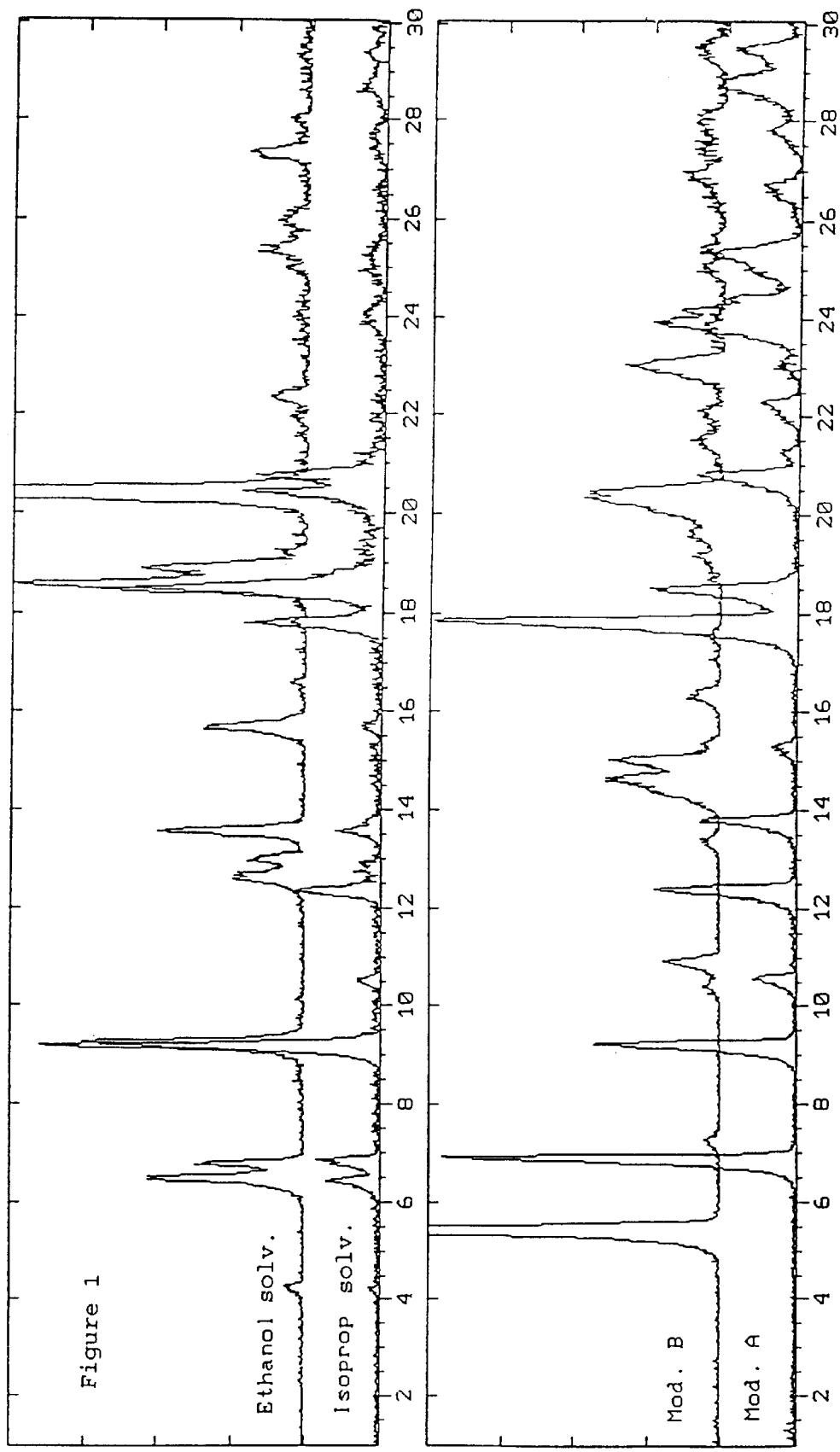
FIG. 1 (upper portion) shows the X-ray diffraction patterns of two solvates of flupirtine maleate.

The lower part of FIG. 1 shows the diffraction patterns of modifications A and B, and Table 1 shows the powder data.

Figure 2:
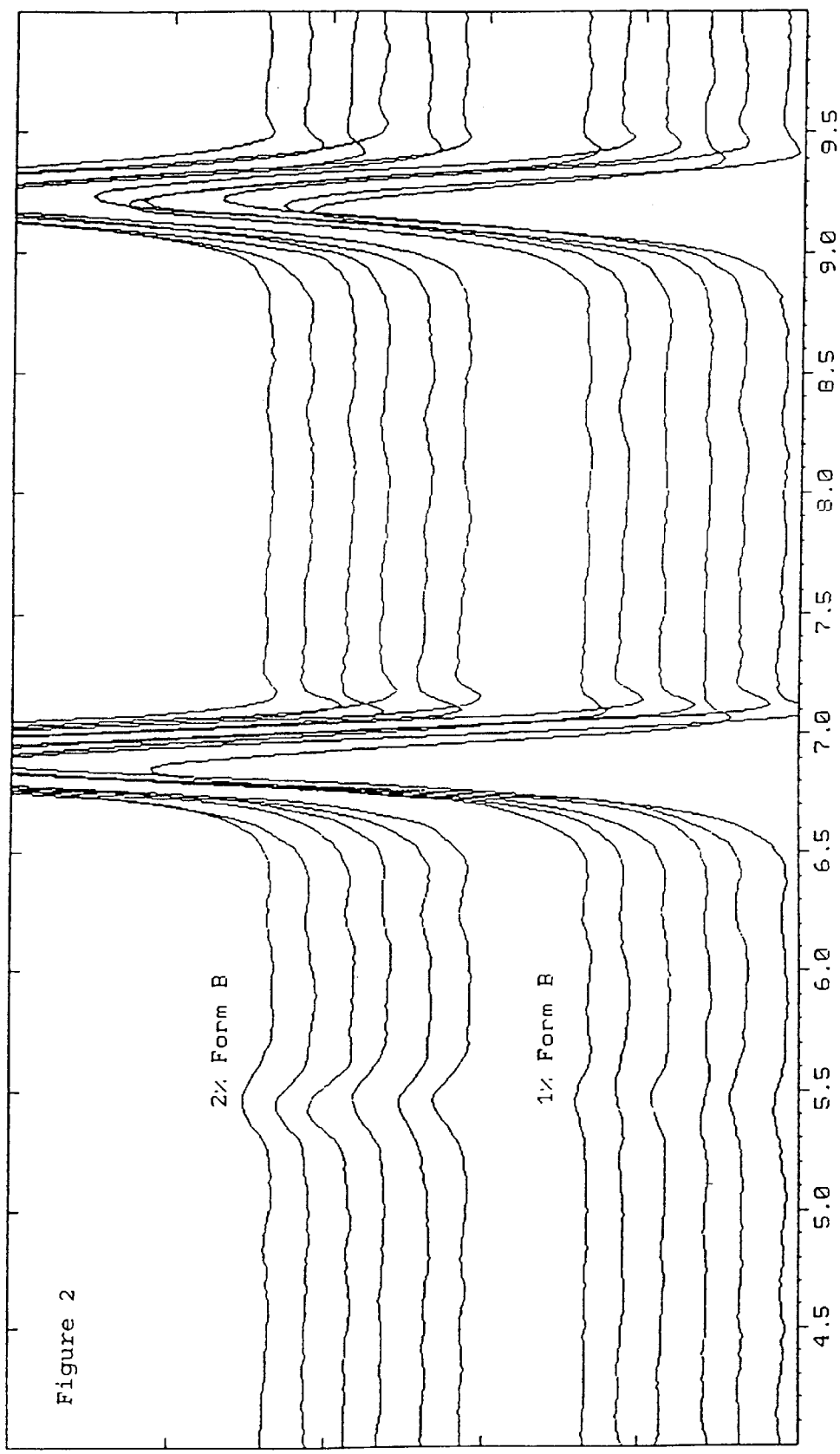
FIG. 2 shows the limit of detection for modification B.

Both modifications show characteristic reflections which do not coincide with the reflection of the respective other modification. These are in particular the strong reflections at 6.9, 9.2 and 17.9°2 l in the case of the A modification and in particular the strongest reflection at 5.5°2 l in the case of the B modification. The limit of detection for the B modification is ≦1% (FIG. 2).

TABLE 1 powder data of the modifications of flupirtine maleate

| A modification | | | B modification | | |
|---|---|---|---|---|---|
| 2θ (°) | d value (Å) | Intensity (%) | 2θ (°) | d value (Å) | Intensity (%) |
| | | | 5.46 | 16.2 | 100 |
| 6.90 | 12.8 | 98 | | | |
| | | | 7.28 | 12.1 | 3 |
| 9.22 | 9.6 | 55 | | | |
| 10.57 | 8.36 | 11 | 10.43 | 8.48 | 3 |
| | | | 10.91 | 8.10 | 10 |
| 12.39 | 7.14 | 38 | | | |
| | | | 13.42 | 6.59 | 3 |
| 13.81 | 6.41 | 25 | | | |
| | | | 14.44 | 6.13 | 13 |
| | | | 14.66 | 6.04 | 20 |
| | | | 15.04 | 5.89 | 20 |
| 15.32 | 5.78 | 7 | 15.40 | 5.75 | 2 |
| | | | 16.37 | 5.41 | 4 |
| | | | 17.60 | 5.04 | 1 |
| 17.85 | 4.97 | 100 | | | |
| 18.50 | 4.79 | 39 | | | |
| | | | 18.70 | 4.74 | 3 |
| | | | 19.16 | 4.63 | 5 |
| | | | 19.58 | 4.53 | 6 |
| | | | 20.08 | 4.42 | 13 |
| | | | 20.34 | 4.36 | 24 |
| | | | 20.44 | 4.34 | 24 |
| 20.81 | 4.27 | 28 | | | |
| 21.26 | 4.18 | 5 | | | |
| | | | 21.52 | 4.13 | 6 |
| 21.92 | 4.05 | 5 | | | |
| 22.30 | 3.99 | 11 | 22.11 | 4.02 | 5 |
| 23.03 | 3.86 | 7 | 23.02 | 3.86 | 17 |
| 23.90 | 3.72 | 40 | 23.84 | 3.73 | 2 |
| 24.15 | 3.68 | 32 | | | |
| 24.41 | 3.64 | 20 | | | |
| 24.98 | 3.56 | 15 | 25.07 | 3.55 | 3 |
| 25.35 | 3.51 | 27 | 25.48 | 3.49 | 4 |
| 26.68 | 3.34 | 9 | | | |
| | | | 26.97 | 3.30 | 7 |
| | | | 27.48 | 3.24 | 4 |
| 27.81 | 3.21 | 10 | 28.00 | 3.19 | 5 |
| 28.71 | 3.11 | 23 | | | |
| 29.51 | 3.03 | 18 | 29.45 | 3.03 | 3 |
| | | | 30.28 | 2.95 | 3 |
| 30.55 | 2.92 | 17 | | | |

Diffraction Patterns of the Solvates

The upper part of FIG. 1 shows the two solvates of flupirtine maleate.

The diffraction patterns of the solvates differ from those of modifications A and B in particular in the occurrence of additional reflections. Solvate is detectable alongside the two modifications in particular from the reflection at 6.4°2 l (d=13.7 Å). The B modification is detectable alongside solvate whereas small proportions of the A modification are not detected alongside solvate. The relationship between the diffraction patterns of the solvates and the diffraction pattern of the A modification indicates that the intracrystalline solvent incorporation takes place during the nucleation of the A modification.

Thermal Reactions of the Crystal Phases

Figure 3:
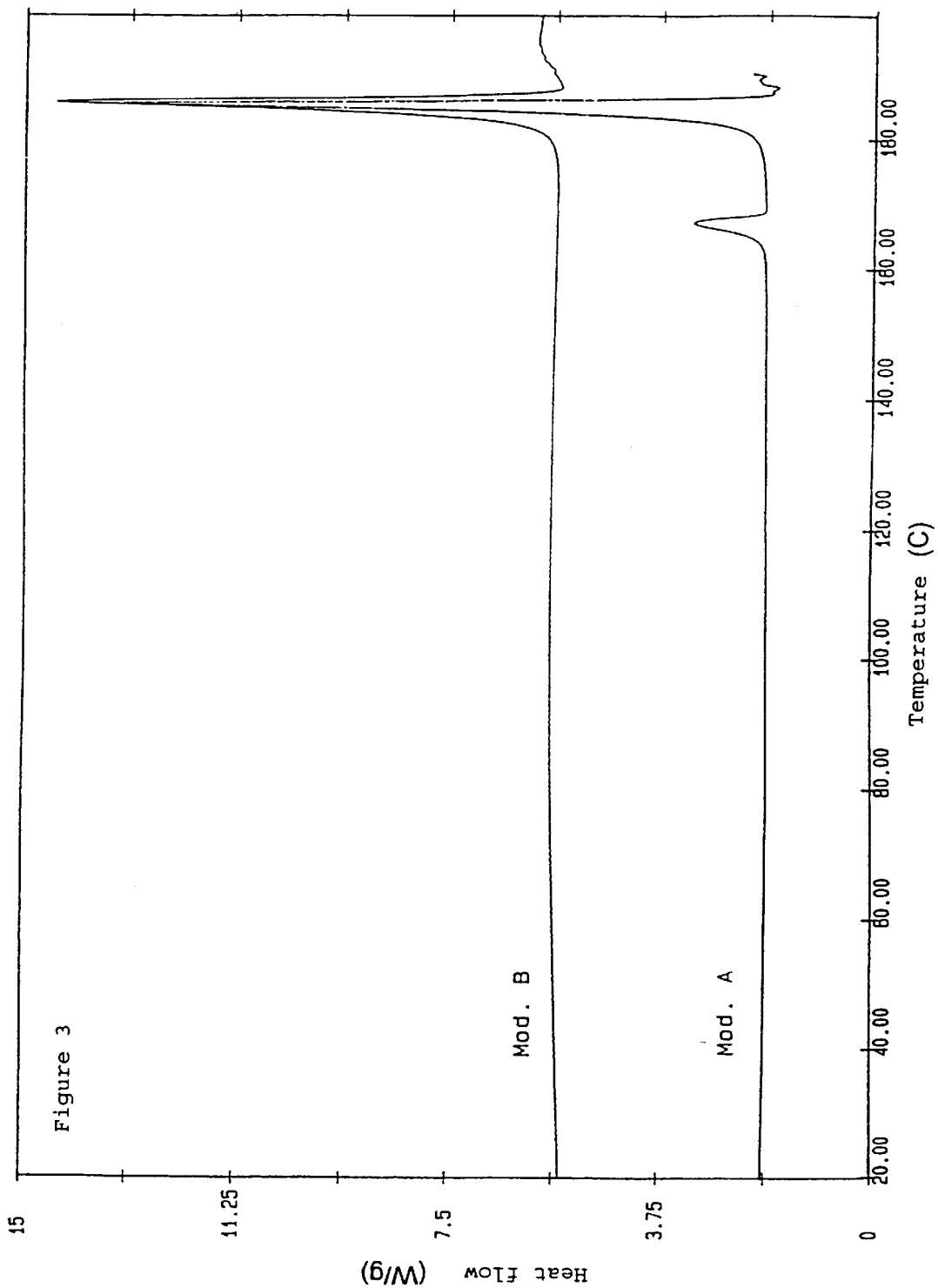
FIG. 3 shows the differential scanning calorimetry curves of modifications A and B.

Methods:
Differential scanning calorimetry (DSC)
Thermal gravimetry (TG)
Temperature-controlled X-ray diffractometry FIG. 3 shows the DSC curves of the two modifications. The A modification undergoes two endothermic reactions, that is to say the transformation point A→B at 164° C. (onset) and the melting point for the B modification at 184° C. (onset). The B modification shows only one endothermic effect at 184° C., which indicates melting.

Figure 4:
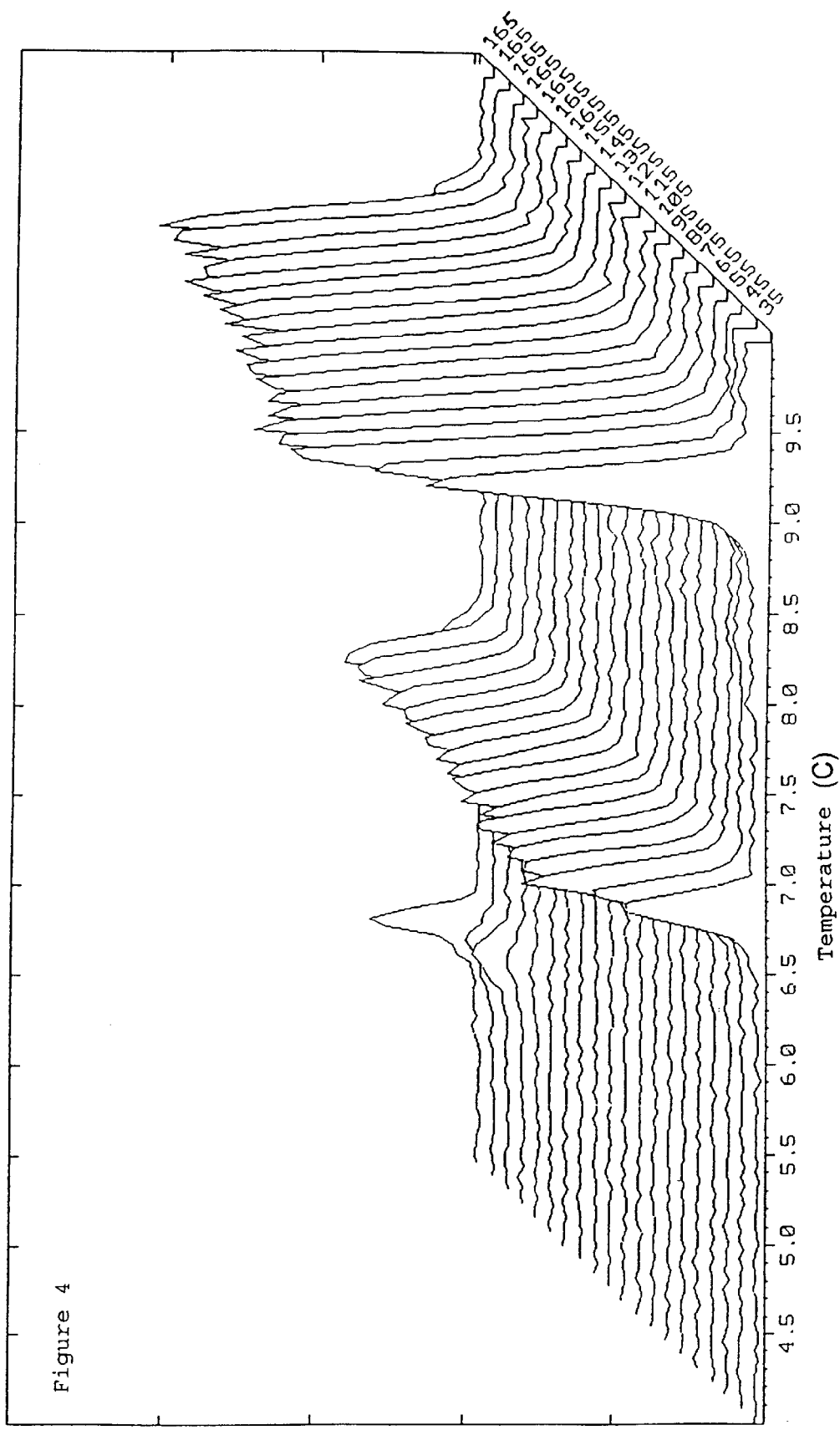
FIG. 4 shows the thermal lattice transformation A→B.

FIG. 4 shows the thermal lattice transformation A→B. In agreement with the DSC result, the strong reflection of the B modification at 5.5°2 l appears at 165° C.

Figure 5:
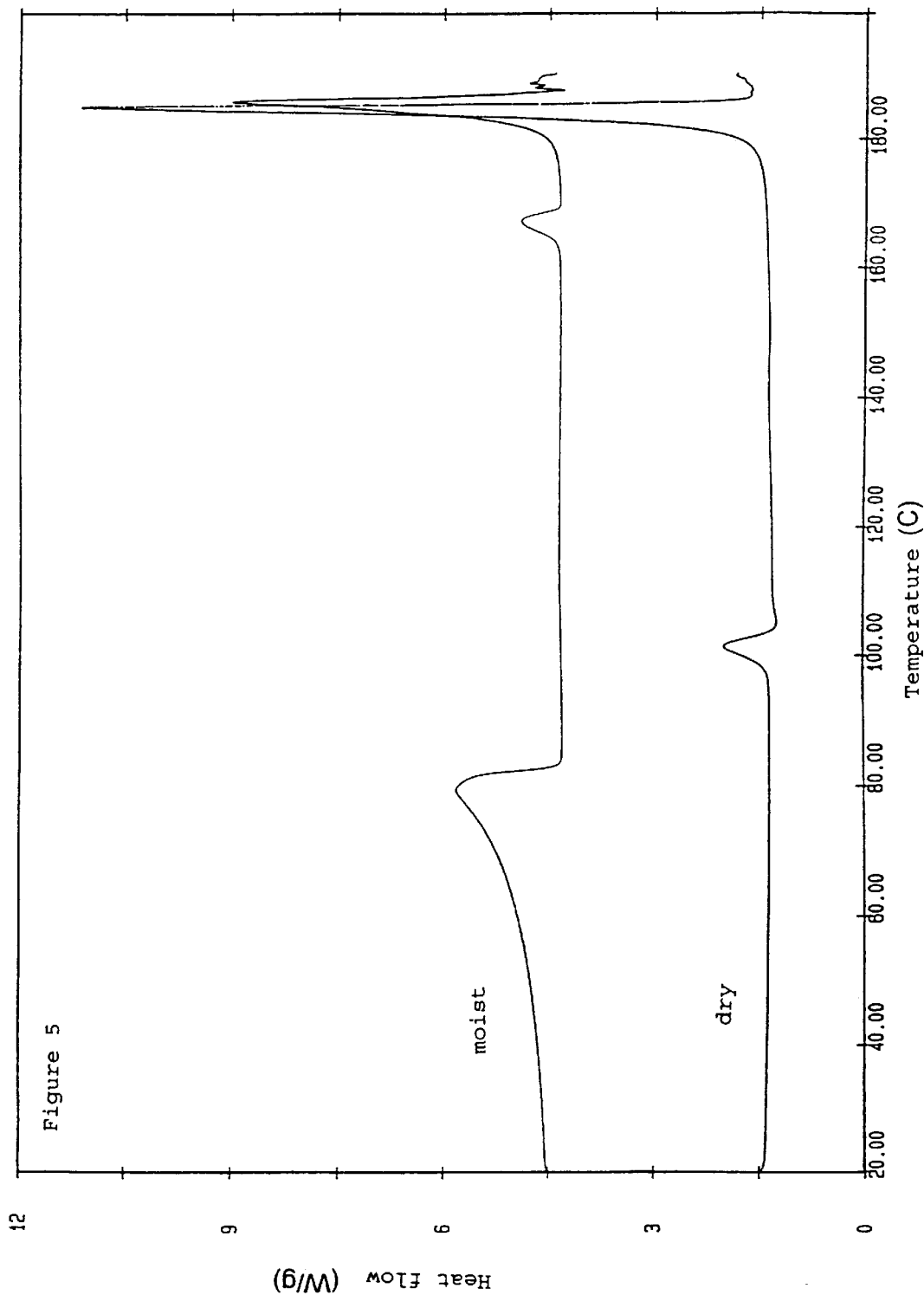
FIGS. 5 and 6 show the different courses of the crystal reactions on heating solvent-moist and pre-dried crystals.
Figure 6:
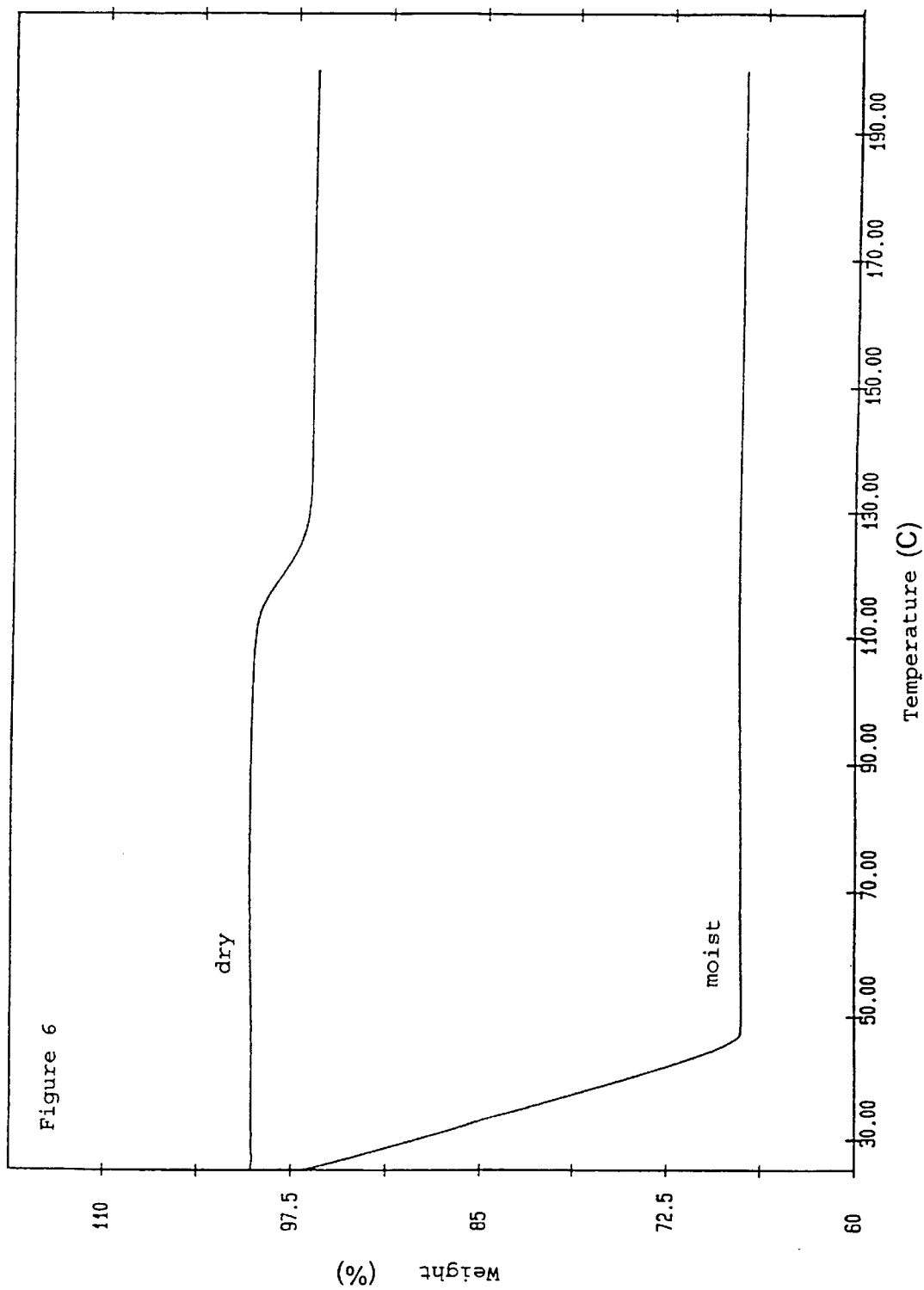

FIGS. 5 and 6 show the different courses of the crystal reactions on heating solvent-moist and predried crystals, taking crystals obtained from isopropanol as an example. In the moist state, desolvation occurs together with release of the externally bound solvent with formation of the A modification, which is then converted into the B modification at 164° C.

In the dry state, the dehydration takes place at substantially higher temperature with formation of the B modification.

Figure 7:
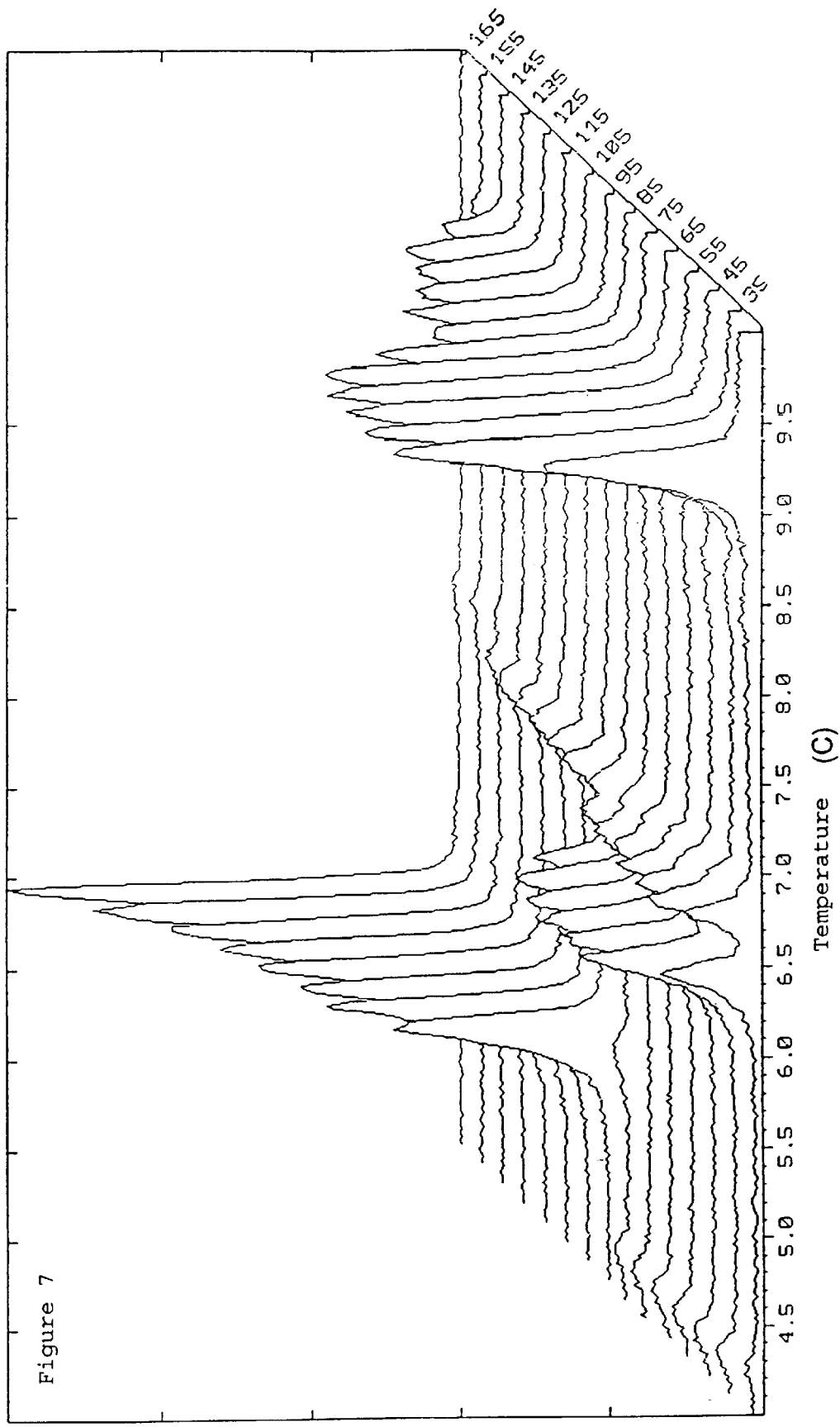
FIG. 7 shows the thermal lattice transformations in the case of crystals obtained from isopropanol.

FIG. 7 shows the thermal lattice transformations in the case of crystals obtained from isopropanol. Initially, solvate (6.4°2 l) is present alongside the A modification. At 95° C., the characteristic solvate reflection disappears and the characteristic reflection of the B modification at 5.5°2 l appears. On further heating, the characteristic reflections of the A modification at 6.9 and 9.2°2 l also disappear while the intensity of the B reflection increases greatly.

The process according to the invention for the preparation of pure flupirtine maleate and of the pure A modification of flupirtine maleate has the following decisive advantages:

In process step A, the unacceptable solvent 2-methoxyethanol is replaced by water-soluble alcohols, such as isopropanol or ethanol.

In the same process step, the reaction time of the N-acylation can be reduced from two hours to half an hour, resulting in a reduction in the range of by-products and in the concentration of troublesome coloured complexes.

The complicated purification steps C–E of the flupirtine process used to date are dispensed with. The crude maleate can be converted into pure flupirtine maleate by a problem-free purification process or the preparation of the pure flupirtine maleate is effected directly from the flupirtine base formed in situ.

The temperature for the establishment of the pure crystal modification was reduced from a range of 60 to 65° C. to a range of −10 to 60° C.

It was possible for the first time to prepare the pure A modification of flupirtine maleate.

The process according to the invention is to be illustrated in more detail with reference to examples:

1st Example

Preparation of Pure Flupirtine Maleate 75 g (0.286 mol) of ANFP are hydrogenated in a suspension of 12.5 g of Raney nickel in 400 ml of isopropanol at 65° C. and a hydrogen pressure of 5 bar. After hydrogenation is complete, 26.4 ml of ethyl chloroformate and then 50.6 ml of triethylamine are added to the solution. After the addition of a further 6.3 ml of ethyl chloroformate, the reaction solution is stirred for a further hour at 60° C. The hot solution is then sucked, with stirring, into a solution of 53.3 g of maleic acid in 1.5 l of $H_2O$, which solution has been heated to 50–60° C., and the catalyst is rinsed with a little isopropanol.

The flupirtine maleate is precipitated in colourless form and the crystal suspension is cooled to 20° C. with further stirring and is left at this temperature for 20 minutes. The flupirtine maleate is filtered off with suction, rinsed with about 500 ml of water and dried in vacuo at 35° C.

Yield: 107.55 g (89.6% of theory, based on ANFP used).

2nd Example

Preparation of Pure Flupirtine Maleate 18.5 g (0.07 mol) of ANFP are hydrogenated analogously to Example 1 in a suspension of 2.0 g of Raney nickel in 140 ml of ethanol at 60–70° C. and a hydrogen pressure of 5 bar. After hydrogenation is complete, the further reaction is carried out at 40–50° C. with 9.3 g of ethyl chloroformate (0.86 mol) and 9.2 g of triethylamine (0.91 mol). The reaction solution separated from the catalyst is introduced into 540 ml of water with stirring. After stirring has been carried out for 2 hours at room temperature, the precipitated base is filtered off with suction, washed with water and isopropanol and crystallized in 3.7 times the amount of isopropanol.

Yield: 18.4 g (86.0% of theory).

The precipitation and modification of pure flupirtine maleate is carried out according to Examples 7 and 8.

3rd Example

Preparation of the Pure A Modification of Flupirtine Maleate

Figure 8:
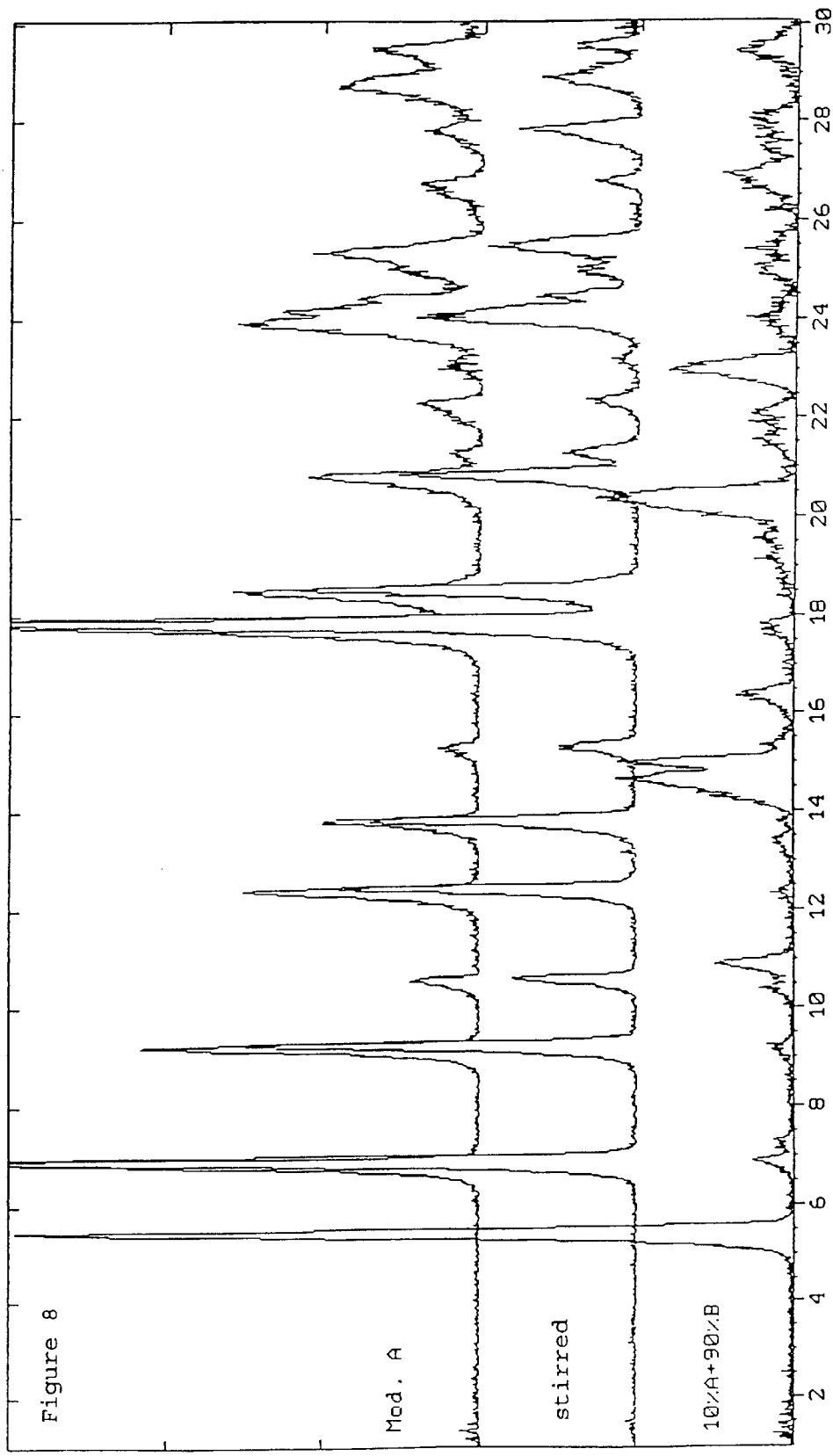
FIG. 8 shows the X-ray diffraction patterns of modification A, a mixture of 10% modification A and 90% modification B, and a mixture of 10% modification A and 90% modification B which has been treated by dispersal into propanol and stirring at 20° C.

Dried flupirtine maleate which was crystallized from isopropanol and contained 10% of the A modification in addition to 90% of the B modification (FIG. 8, bottom curve) was dispersed in isopropanol in a ratio of 1:0.8. After stirring had been carried out for 200 minutes at 20° C., the characteristic strong B reflection at 5.5°2 1 had disappeared and only the characteristic reflections of the A modification at 6.9 and 9.2°2 1 were observed (FIG. 8, middle curve).

4th Example

Dried flupirtine maleate which was crystallized from isopropanol and contained 10% of the A modification in addition to 90% of the B modification was dispersed in isopropanol in a ratio of 1:0.8 and stirred at 35° C. After stirring had been carried out for only 70 minutes, the characteristic strong B reflection at 5.5°2 1 had disappeared and only the characteristic reflections of the A modification at 6.9 and 9.2°2 1 were observed.

5th Example

Figure 9:
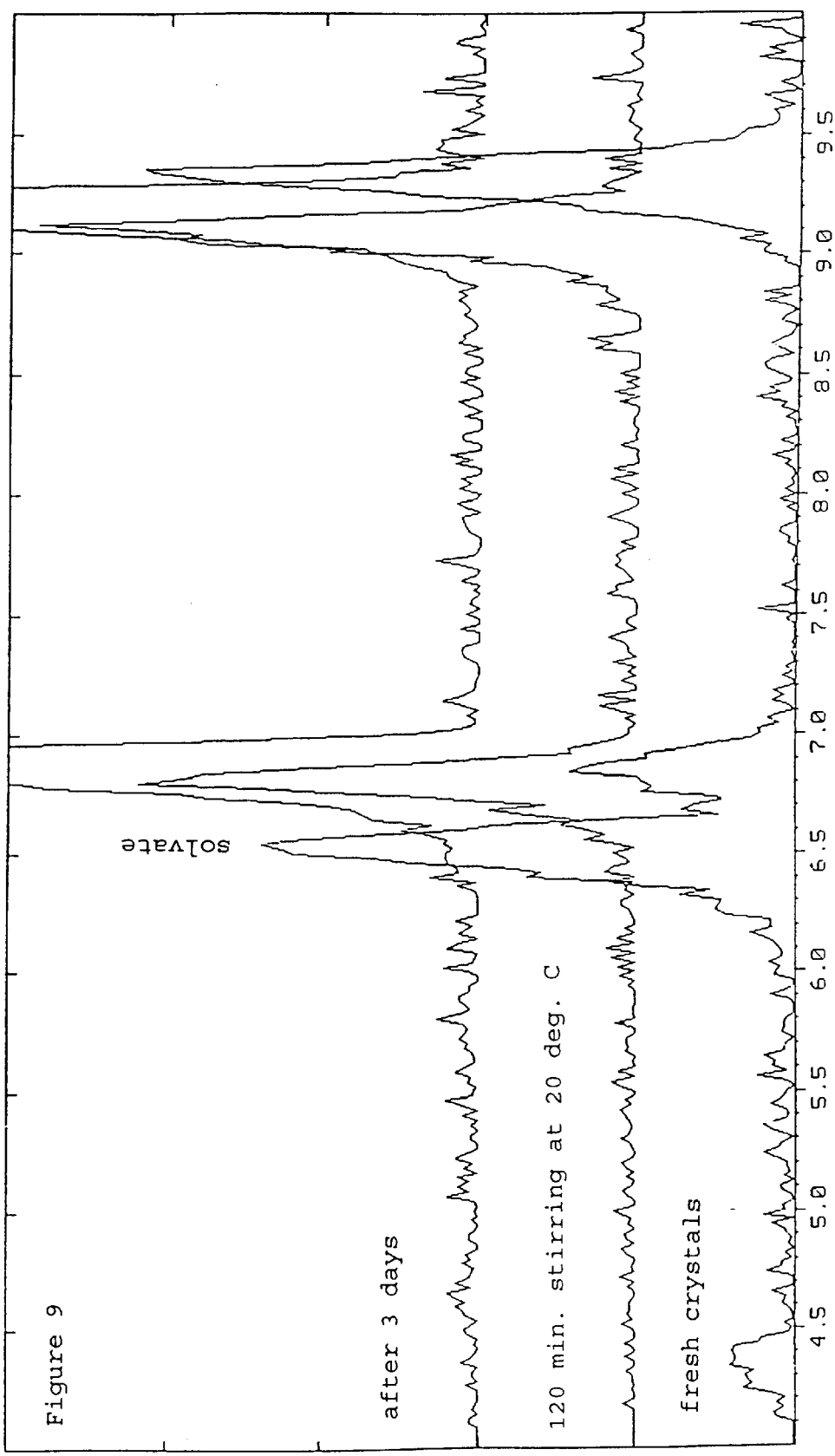
FIG. 9 shows the disappearance of solvate when flupertine maleate was dissolved in isopropanol at 60° C., cooled to 20° C. and stirred.

Slightly less than the maximum soluble amount of flupirtine maleate was completely dissolved in isopropanol at 60° C., slowly cooled to 20° C. and then stirred at 20° C. Before the beginning of stirring, solvate was observed in addition to the A modification (FIG. 9, bottom curve). After 120 minutes, only the A modification was detectable (FIG. 9, middle curve). No reformation of solvate was observed even after the suspension was allowed to stand for 3 days (FIG. 9, top curve).

6th Example

Slightly less than the maximum soluble amount of flupirtine maleate was completely dissolved at 60° C. in isopropanol which contained 5% of water, cooled to 20° C. and then stirred at 20° C. Before the beginning of stirring, solvate was present in addition to the A modification. After stirring had been carried out for 130 minutes, only the A modification was detectable.

7th Example

Figure 10:
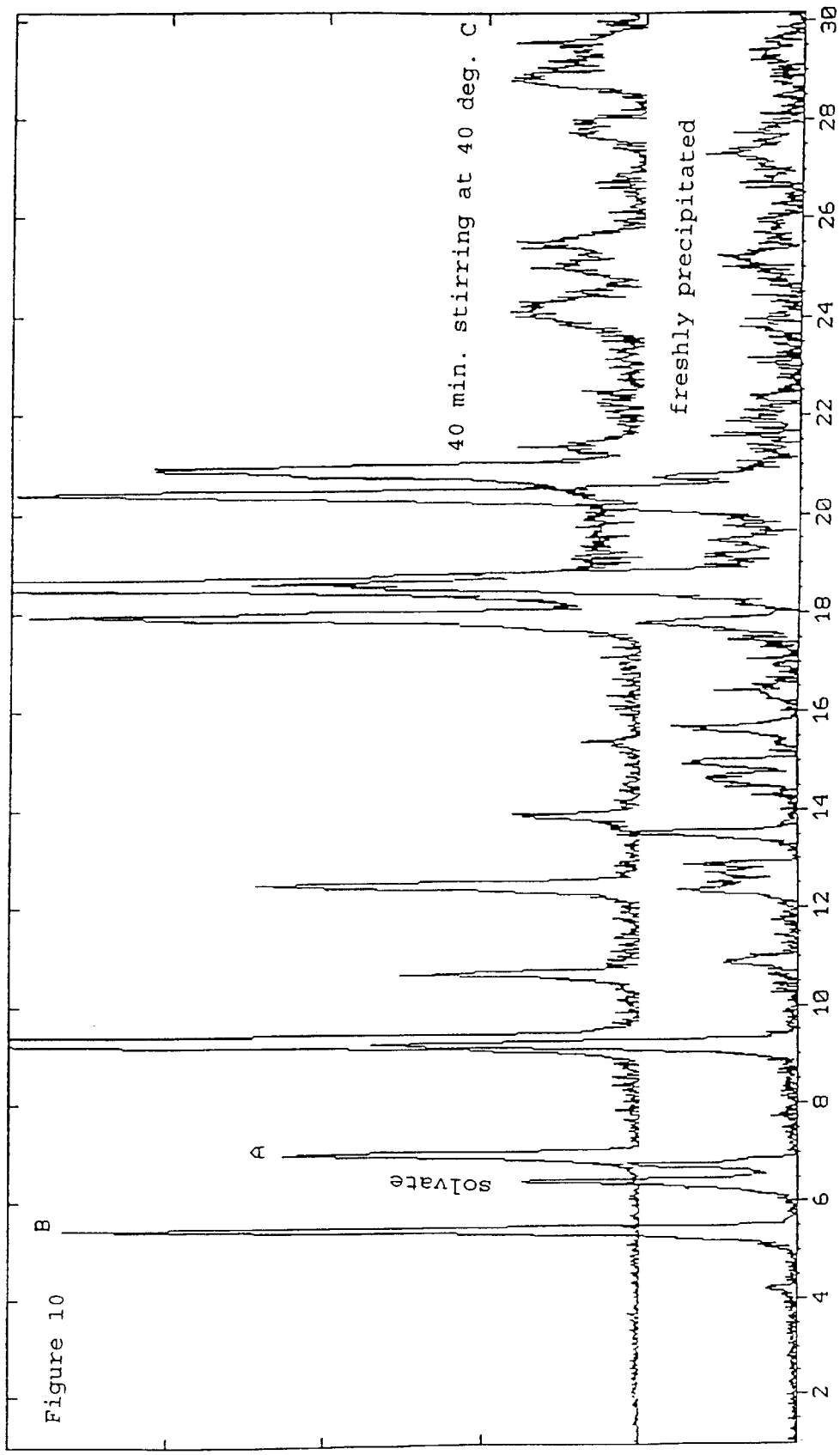
FIG. 10 shows the conversion of solvate and modification B into modification A upon stirring in isopropanol at 40° C.

Stoichiometric amounts of flupirtine base and of maleic acid were dissolved in isopropanol at 50° C. The precipitation of the flupirtine maleate was carried out by dropwise addition of the maleic acid solution to the solution of the base at 40° C. The freshly precipitated crystals contained solvate in addition to the B modification (FIG. 10, lower curve). After stirring had been carried out for only 40 minutes at 40° C., both the solvate and the B modification had been completely converted into the A modification (FIG. 10, upper curve).

8th Example

Figure 11:
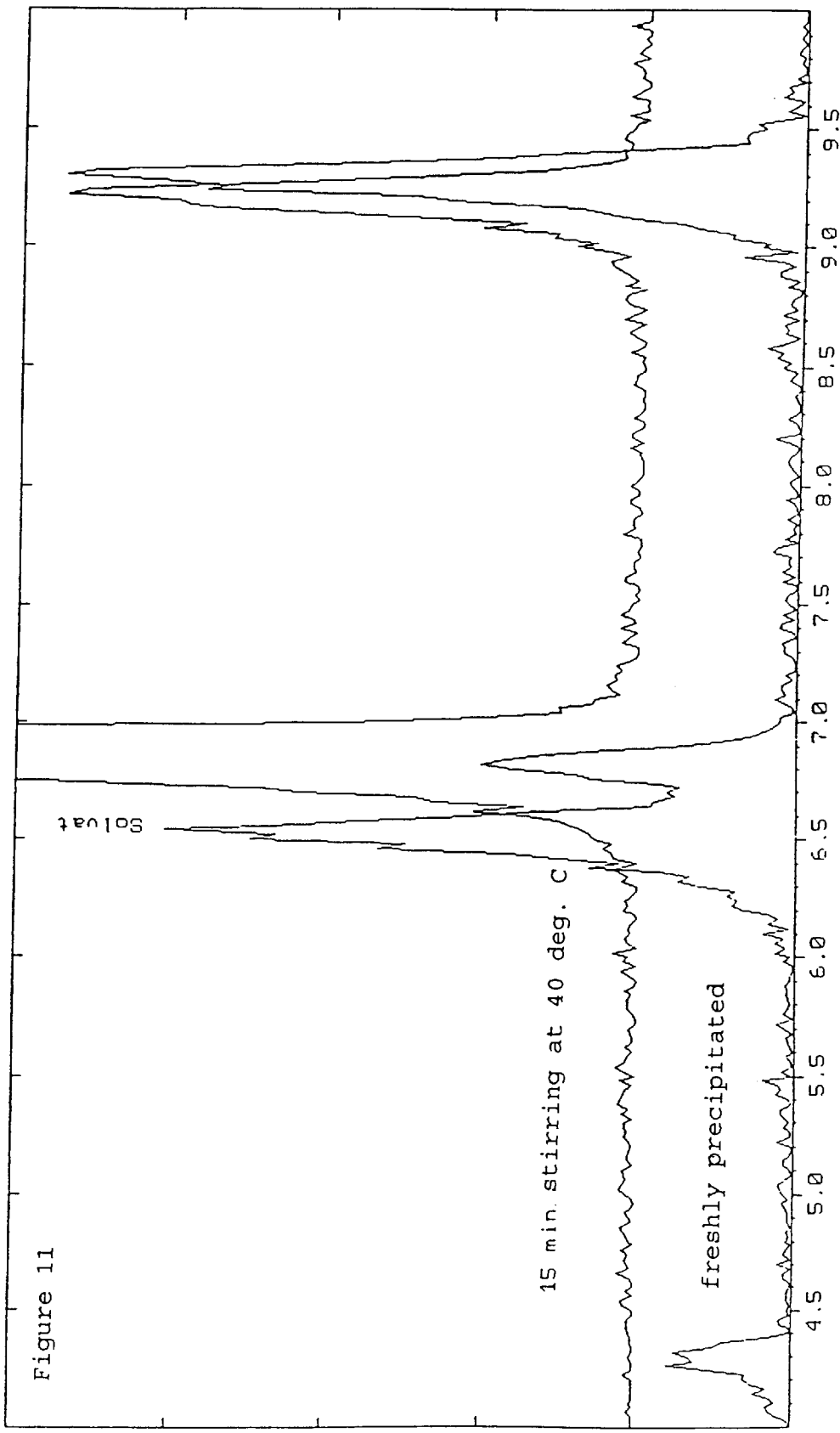
FIG. 11 shows the conversion of solvate into modification A upon stirring in ethanol at 40° C.

Stoichiometric amounts of flupirtine base and of maleic acid were dissolved in ethanol at 40° C. The precipitation of the flupirtine maleate was carried out by dropwise addition of the maleic acid solution to the solution of the base at 40° C. In the freshly prepared crystals, only solvate was detectable (FIG. 11, lower curve). After stirring had been carried out for only 15 minutes at 40° C., the solvate had been completely converted into the A modification (FIG. 11, upper curve).

What is claimed is:

1. A process for the preparation of pure flupirtine maleate comprising the steps of hydrogenation of 2-amino-3-nitro-6-(4-fluorobenzylamino)pyridine in the presence of Raney nickel;

acylation of the resulting product with ethyl chloroformate; and reaction of the resulting flupirtine base with maleic acid to obtain flupirtine maleate;

wherein hydrogenation, acylation and precipitation are carried out in water soluble alcohols.

2. The process according to claim 1 wherein the alcohol is ethanol or isopropanol.

3. The process according to claim 1 wherein either (a) crude flupirtine maleate is isolated and converted to pure flupirtine maleate; or (b) flupirtine maleate is precipitated by reacting flupirtine base formed in situ with maleic acid, and is converted into pure flupirtine maleate without isolation; or (c) crude flupirtine base is precipitated and recrystallized and is then reacted with maleic acid to form pure flupirtine maleate.

4. The process according to claim 1, wherein the reaction is carried out at a temperature between −10° C. and 60° C.

5. The process according to claim 2, wherein the reaction is carried out at a temperature between −10° C. and 60° C.

6. The process according to claims 3, wherein the reaction is carried out at a temperature between −10° C. and 60° C.

7. The process according to one of claims 1–3 further comprising the step of stirring the flupirtine maleate in an ethanol or isopropanol solution, said solution optionally containing water.

8. The process according to claim 1, wherein flupirtine maleate is initially obtained according to step (c) of claim 10.

9. The process according to claim 7, wherein stirring is carried out at a temperature between −10° C. and 60° C.

10. The process according to claim 8, wherein stirring is carried out at a temperature between −10° C. and 60° C.

11. A pure A modification of flupirtine maleate which is obtained according to claim 7.

* * * * *